United States Patent
Govari

(10) Patent No.: US 12,082,875 B2
(45) Date of Patent: Sep. 10, 2024

(54) BALLOON CATHETER HAVING A COIL FOR SENSING TISSUE TEMPERATURE AND POSITION OF THE BALLOON

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd, Yokneam (IL)

(*) Notice: Subject to any disclaimer, the term of this patent is extended or adjusted under 35 U.S.C. 154(b) by 214 days.

(21) Appl. No.: 17/031,711

(22) Filed: Sep. 24, 2020

(65) Prior Publication Data

US 2022/0087737 A1     Mar. 24, 2022

(51) Int. Cl.
*A61B 18/14* (2006.01)
*A61B 17/00* (2006.01)
(Continued)

(52) U.S. Cl.
CPC .......... *A61B 18/1492* (2013.01); *A61B 34/20* (2016.02); *A61B 2017/00526* (2013.01); *A61B 2018/0022* (2013.01); *A61B 2018/00232* (2013.01); *A61B 2018/00375* (2013.01); *A61B 2018/00577* (2013.01); *A61B 2018/00791* (2013.01); *A61B 2018/00821* (2013.01);
(Continued)

(58) Field of Classification Search
CPC .. A61B 2017/00526; A61B 2018/0022; A61B 2018/00232; A61B 2018/00375; A61B 2018/00791; A61B 2018/00821; A61B 2018/1435; A61B 2018/1467; A61B 18/1492; A61B 34/20; A61B 2034/2051
See application file for complete search history.

(56) References Cited

U.S. PATENT DOCUMENTS 4,699,147 A    10/1987   Chilson et al.
4,940,064 A    7/1990    Desai
(Continued)

FOREIGN PATENT DOCUMENTS

CN   111248993 A   6/2020
CN   111248996 A   6/2020
(Continued)

OTHER PUBLICATIONS

Partial European Search Reported dated Feb. 9, 2022, from corresponding European Application No. 21198479.4.
(Continued)

*Primary Examiner* — Daniel W Fowler
*Assistant Examiner* — Bradford C. Blaise
(74) *Attorney, Agent, or Firm* — Troutman Pepper Hamilton Sanders LLP

(57) ABSTRACT

A catheter includes an inflatable balloon for insertion into an organ of a patient, one or more electrodes and a coil. The one or more electrodes are disposed on a surface of the inflatable balloon and are configured to be placed in contact with tissue of the organ, and to perform at least one of: (i) sensing one or more electrical signals from the tissue, and (ii) applying one or more ablation pulses to the tissue. The coil is disposed on the surface of the inflatable balloon, and is configured to output a signal indicative of at least one of: (i) a temperature of the tissue, and (ii) a magnetic field indicative of a position of the catheter in the organ.

18 Claims, 3 Drawing Sheets

(51) Int. Cl.
*A61B 18/00* (2006.01)
*A61B 18/12* (2006.01)
*A61B 34/20* (2016.01)

(52) U.S. Cl.
CPC . *A61B 2018/126* (2013.01); *A61B 2018/1435* (2013.01); *A61B 2018/1467* (2013.01); *A61B 2034/2051* (2016.02)

(56) References Cited

U.S. PATENT DOCUMENTS

| | | |
|---|---|---|
| 5,215,103 A | 6/1993 | Desai |
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,391,199 A | 2/1995 | Ben-Haim |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,119,030 A | 9/2000 | Morency |
| 6,216,043 B1 | 4/2001 | Swanson et al. |
| 6,216,044 B1 | 4/2001 | Kordis |
| 6,239,724 B1 | 5/2001 | Doron et al. |
| 6,332,089 B1 | 12/2001 | Acker et al. |
| 6,428,537 B1 | 8/2002 | Swanson et al. |
| 6,456,864 B1 | 9/2002 | Swanson et al. |
| 6,484,118 B1 | 11/2002 | Govari |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,618,612 B1 | 9/2003 | Acker et al. |
| 6,690,963 B2 | 2/2004 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,001,383 B2 | 2/2006 | Keidar |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 8,998,893 B2 * | 4/2015 | Avitall ............... A61B 18/1492 606/41 |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |

(56) References Cited

U.S. PATENT DOCUMENTS

| | | |
|---|---|---|
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2004/0147852 A1* | 7/2004 | Brister ............... A61B 1/00082 600/549 |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2009/0301643 A1* | 12/2009 | Tilson ............... A61B 17/8827 156/212 |
| 2010/0174282 A1 | 7/2010 | Demarais et al. |
| 2010/0204560 A1* | 8/2010 | Salahieh ............. A61B 5/01 606/41 |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0058197 A1 | 2/2014 | Salahieh et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0216591 A1* | 8/2015 | Cao ............... A61B 18/1492 606/41 |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228061 A1* | 8/2016 | Källbäck ............. A61B 5/0215 |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0333125 A1* | 11/2017 | Lepak ............... A61B 1/015 |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0180684 A1* | 6/2018 | Govari ............... G01R 33/0052 |
| 2018/0184982 A1 | 7/2018 | Basu et al. |
| 2018/0192958 A1 | 7/2018 | Wu |
| 2018/0193090 A1 | 7/2018 | De La Rama |
| 2018/0206792 A1 | 7/2018 | Auerbach et al. |

(56) References Cited

U.S. PATENT DOCUMENTS

| | | |
|---|---|---|
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1* | 12/2018 | Bar-Tal ............... A61B 90/39 |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0232055 A1 | 8/2019 | Deem et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2019/0350489 A1 | 11/2019 | Ludwin et al. |
| 2020/0000518 A1 | 1/2020 | Kiernan et al. |
| 2020/0001054 A1 | 1/2020 | Jimenez et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0069364 A1 | 3/2020 | Salahieh et al. |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0155224 A1 | 5/2020 | Bar-Tal |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0022803 A1* | 1/2021 | Olson ............... A61B 18/1492 |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 9421167 A1 | 9/1994 |
| WO | 9421169 A1 | 9/1994 |
| WO | WO 96/05768 A1 | 2/1996 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |

(56) References Cited

FOREIGN PATENT DOCUMENTS

| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |
| WO | 2020206328 A1 | 10/2020 |

OTHER PUBLICATIONS

Extended European Search Reported dated May 11, 2022, from corresponding European Application No. 21198479.4.

* cited by examiner

BALLOON CATHETER HAVING A COIL FOR SENSING TISSUE TEMPERATURE AND POSITION OF THE BALLOON

FIELD OF THE INVENTION

The present invention relates generally to medical devices, and particularly to techniques for incorporating and using position and temperature sensors in balloon catheters having a diameter smaller than 10 mm.

BACKGROUND OF THE INVENTION

Various types of diagnostic and therapeutic catheters, such as balloon catheters, may be used in mapping and/or treatment applications, such as in cardiac high-resolution cardiac ablation.

For example, U.S. Patent Application Publication 2019/0350489 describes a method including, in a processor, receiving position signals that are indicative of positions of (i) multiple electrodes disposed on an inflatable balloon fitted at a distal end of a catheter, and (ii) first and second electrodes fitted on a shaft of the catheter, on either side of the balloon. The positions of the multiple electrodes disposed on the balloon are calculated based on the received position signals and based on a known distance between the first and second electrodes.

U.S. Pat. No. 7,001,383 describes a method for ablating tissue in a heart of a subject during an ablation procedure. The method includes applying a local treatment to the heart at a plurality of sites designated for ablation. At each respective site, a parameter is sensed that is indicative of a level of ablation at the site. The method preferably includes displaying a map of the heart, and designating, on the map, during the ablation procedure, indications of the respective levels of ablation at the sites, responsive to the respective sensed parameters.

SUMMARY OF THE INVENTION

An embodiment of the present invention that is described herein provides a catheter including an inflatable balloon for insertion into an organ of a patient, one or more electrodes and a coil. The one or more electrodes are disposed on a surface of the inflatable balloon and are configured to be placed in contact with tissue of the organ, and to perform at least one of: (i) sensing one or more electrical signals from the tissue, and (ii) applying one or more ablation pulses to the tissue. The coil is disposed on the surface of the inflatable balloon, and is configured to output a signal indicative of at least one of: (i) a temperature of the tissue, and (ii) a magnetic field indicative of a position of the catheter in the organ.

In some embodiments, the inflatable balloon has diameter smaller than 10 mm at an inflated position. In other embodiments, the coil includes a magnetic sensor, which is configured to sense the magnetic field for sensing the position of the catheter in the organ. In yet other embodiments, the coil includes a resistance temperature detector (RTD), which is configured to output the signal indicative of the temperature of the tissue.

In an embodiment, the catheter includes one or more thermocouples, which are coupled to the surface of the inflatable balloon, and are configured to output an additional signal indicative of the temperature of the tissue. In another embodiment, the catheter includes a flexible printed circuit board (PCB) wrapped around the surface of the inflatable balloon. In yet another embodiment, the one or more electrodes and the coil are connected to electrical traces of the flexible PCB.

There is additionally provided, in accordance with an embodiment of the present invention, a catheter, including an inflatable balloon for insertion into an organ of a patient, one or more electrodes, and one or more thermocouples. The one or more electrodes are disposed on a surface of the inflatable balloon and are configured to be placed in contact with tissue of the organ, and to perform at least one of: (i) sensing one or more electrical signals from the tissue, and (ii) applying one or more ablation pulses to the tissue. The one or more thermocouples are coupled to the surface of the inflatable balloon for sensing the temperature of the tissue.

In some embodiments, the one or more electrodes and the one or more thermocouples are connected to electrical traces of the flexible PCB.

There is further provided, in accordance with an embodiment of the present invention, a method for producing a catheter, the method including receiving a flexible substrate including electrical interconnections formed on a first layer. A coil is formed on a second layer of the flexible substrate, and the ends of the coil are connected to the electrical interconnections. One or more electrical devices are coupled to the flexible substrate and the electrical devices are connected to the electrical interconnections. The flexible substrate is wrapped around an inflatable balloon, and the inflatable balloon is coupled to a distal end of a shaft of the catheter.

In some embodiments, receiving the flexible substrate includes receiving a printed circuit board (PCB), and the electrical interconnections include electrical traces of the PCB. In other embodiments, forming the coil includes printing a spiral-shaped trace or a serpentine-shaped trace. In yet other embodiments, coupling the one or more electrical devices includes coupling at least one of: (i) one or more electrodes, and (ii) one or more thermocouples.

There is additionally provided, in accordance with an embodiment of the present invention, a catheter including an expandable balloon, one or more electrodes, and at least one coil. The expandable balloon defining a longitudinal axis extending through the balloon, the balloon having a compound curved surface of revolution about the longitudinal axis. The one or more electrodes are disposed on the compound curved surface of the expandable balloon and are configured to be placed in contact with tissue of the organ, and to perform at least one of: (i) sensing one or more electrical signals from the tissue, and (ii) applying one or more ablation pulses to the tissue. The at least one coil is defining a coil axis extending at an angle to the longitudinal axis of the balloon, the at least one coil being disposed on the compound curved surface of the expandable balloon.

In some embodiments, the balloon includes a distal toroidal-like surface portion approximating a circular toroid and a proximal hemisphere-like surface portion approximating a truncated hemispherical surface, the at least one coil being disposed on the compound curved surface of both the toroidal-like portion and hemisphere like portion of the balloon. In other embodiments, the at least one coil is disposed on the compound curved surface of the balloon that does not have an electrode mounted thereon. In an embodiment, the at least one coil is disposed between an electrode and the compound curved surface of the balloon. In another embodiment, the electrode includes cut outs to allow the coil under the electrode to be exposed to the ambient environment.

The present invention will be more fully understood from the following detailed description of the embodiments thereof, taken together with the drawings in which:

DETAILED DESCRIPTION OF EMBODIMENTS

Overview

Small-diameter balloon catheters, such as a balloon having a diameter of about 9 mm, may be used for high-resolution mapping and ablation when treating arrhythmia (i) in a patient heart, or (ii) in other suitable organs of the patient. In such procedures, it is important, to receive in real-time, inter alia, high-resolution sensing of: (i) position and orientation of the balloon catheter in patient heart, and (ii) temperature of the ablated tissue and/or ablating electrodes. Due to the small diameter of the balloon, there is great difficulty in incorporating sensors configured to fulfill the above functions.

An embodiment of the present invention that is described herein provides a catheter comprising an inflatable balloon having a diameter smaller than 10 mm for insertion into an organ (e.g., heart) of a patient, one or more electrodes, and one or more coils.

In some embodiments, the electrodes are coupled to or formed in a flexible printed circuit board (PCB), which is wrapped on and coupled to a surface of the inflatable balloon. The electrodes are configured to be placed in contact with tissue at a target location of the heart, and to perform at least one of: (i) sensing one or more electrical signals from the tissue, and (ii) applying one or more ablation pulses to the tissue.

In some embodiments, a system for ablating tissue of the patient heart comprises a magnetic position tracking system having multiple (e.g., three) field generators, placed at known positions external to patient and configured to apply magnetic fields to a region-of-interest of the patient heart.

In some embodiments, the coil of the catheter is patterned in or coupled to the flexible PCB of the inflatable balloon, and is configured to output a signal indicative of the temperature of at least the tissue, and/or a magnetic field indicative of the position of the catheter in the patient heart. In the first embodiment, the coil comprises a resistance temperature detector (RTD).

In some embodiments, the system comprises a processor, which is configured to receive signals from the electrodes and the coil, and based on instructions from a physician performing the ablation and the received signals, the processor is configured to control the ablation procedure.

In other embodiments, instead of one or more of the coils, the balloon catheter may comprise one or more thermocouples, which are coupled to the surface of the PCB, and are configured to output an additional signal indicative of the temperature of the tissue and/or the temperature of the one or more electrodes in close proximity to the thermocouple.

In an embodiment, at least one of the coils comprises a planar coil.

The disclosed techniques improve the quality of high-resolution sensing and ablation by enhancing the functionality, e.g., temperature measurement and accurate position and orientation sensing, of small-diameter balloon catheters.

SYSTEM DESCRIPTION

Figure 1:
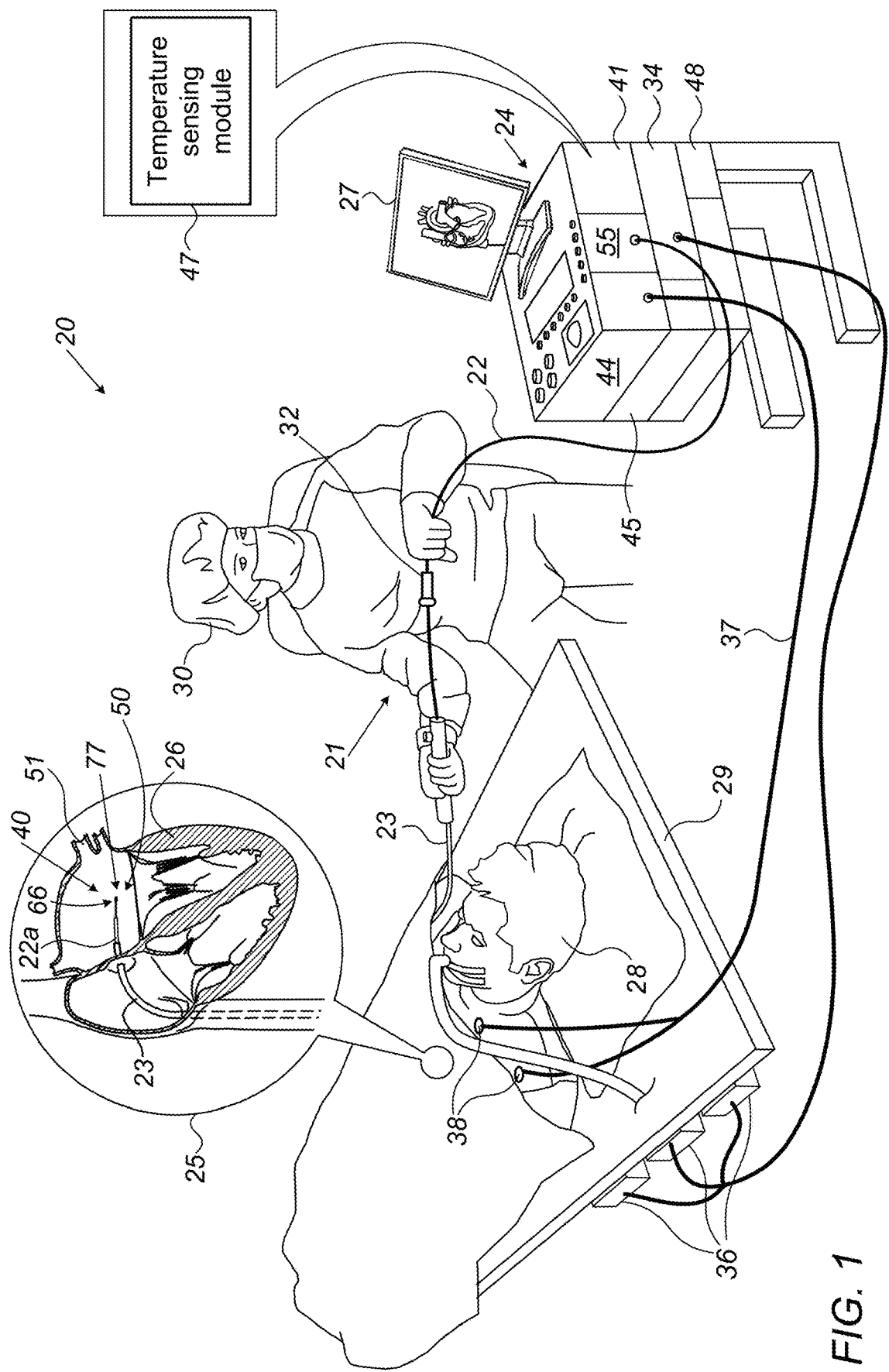
FIG. 1 is a schematic, pictorial illustration of a catheter-based position-tracking and radiofrequency (RF) ablation system, in accordance with an embodiment of the present invention.

FIG. 1 is a schematic, pictorial illustration of a catheter-based position-tracking and radiofrequency (RF) ablation system 20, in accordance with an embodiment of the present invention.

Reference is now made to an inset 25. In some embodiments, system 20 comprises a catheter tip 40 that is fitted at a distal end 22a of a shaft 22 of a catheter 21.

In some embodiments, catheter tip 40 comprises an inflatable balloon 66 having multiple electrodes, such as but not limited to multiple sensing and/or RF ablation electrodes 77 and one or more spiral electrodes 50. Balloon 66 and electrodes 50 and 77 are described in detail in FIG. 2 below.

In some embodiments, at least one spiral electrode 50 is configured to serve as a magnetic sensor and/or as a temperature sensor. In an embodiment described herein, at least one spiral electrode 50 is used for sensing the temperature of tissue of an ostium 51 of a pulmonary vein (PV) in a heart 26. In an embodiment, one or more spiral electrodes 50 can take the form of a circular spiral and/or rectangular spiral, as shown and described in detail in FIG. 2B below.

In some embodiments, the proximal end of catheter 21 is connected to a control console 24 comprising an RF generator 45. An ablation protocol comprising ablation parameters is stored in a memory 48 of console 24.

Reference is now made to the general view of FIG. 1. In some embodiments, a physician 30 inserts distal end 22a of shaft 22 through a sheath 23 into heart 26 of a patient 28 lying on a table 29. Physician 30 advances the distal end of shaft 22 to a target location in heart 26 by manipulating shaft 22 using a manipulator 32 near the proximal end of catheter 21. During the insertion of distal end 22a, catheter tip 40 is maintained inside sheath 23 to minimize vascular trauma along the way to target location.

In an embodiment, physician 30 navigates the distal-end of shaft 22 to the target location by tracking a direction of catheter tip 40. During navigation of distal end 22a in heart 26, console 24 receives signals from spiral electrode 50 at catheter tip 40, which acts as a magnetic sensor in response to magnetic fields from external field generators 36. Magnetic field generators 36 are placed at known positions external to patient 28, e.g., below table 29. Console 24 also comprises a driver circuit 34, configured to drive magnetic field generators 36.

In some embodiments, based on the signal received from spiral electrode 50, a processor 41 of system 20 is configured to estimate the position and orientation of catheter tip 40 in patient heart 26. Processor 41 is further configured to display, e.g., on a display 27 of console 24, at least a marker indicative of the position and orientation of catheter tip 40. In an embodiment, the position and orientation of the marker may be displayed relative to an orientation of an axis of approximate symmetry of ostium 51. In an embodiment, display 27 is configured to display the tracked position of catheter tip 40 overlaid on an anatomical image or model of heart 26.

The method of position tracking using external magnetic fields is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are hereby incorporated by reference in their entirety herein into this application as if set forth in full. In an embodiment, signals from spiral electrode 50 are further used for position sensing using the aforementioned CARTO™ system.

In some embodiments, once distal end 22a of shaft 22 has reached heart 26, physician 30 retracts sheath 23 and further manipulates shaft 22 to navigate catheter tip 40 to an ostium 51 of the pulmonary vein, or to any other target location of heart 26.

In some embodiments, while catheter tip 40 is placed in contact with the tissue, physician 30 controls RF generator 45 to apply pulses of RF electric currents to be passed between electrodes 77 of catheter tip 40 and an indifferent (i.e., neutral) electrode patch that is coupled externally, typically attached to the skin of patient 28. The patch may comprise a single electrode or multiple electrodes, referred to herein as electrodes 38, which are shown connected by wires running in a cable 37. Processor 41 is configured to adjust the parameters of the ablating currents by outputting appropriate instructions to RF generator 45 that generates the currents.

In other embodiments, processor 41 is configured to control RF generator 45 to apply bipolar RF ablation pulses to one or more pairs of electrodes 77 of catheter tip 40.

In some embodiments, processor 41 comprises a temperature sensing module 47, which is configured to receive, from spiral electrode 50, electrical signals conducted by wires running through shaft 22 to processor 41.

Processor 41 is typically a general-purpose computer, with suitable front end and (a) ECG interface circuits 44 for receiving ECG signals from electrodes 38, and (b) electrical interface circuitry 55 for receiving signals from catheter 21, as well as for applying RF energy treatment via catheter 21 in a left atrium of heart 26 and for controlling the other components of system 20. Processor 41 typically comprises a software in a memory 48 of system 20 that is programmed to carry out the functions described herein. The software may be downloaded to the computer in electronic form, over a network, for example, or it may, alternatively or additionally, be provided and/or stored on non-transitory tangible media, such as magnetic, optical, or electronic memory.

This particular configuration of system 20 is shown by way of example, in order to illustrate certain problems that are addressed by embodiments of the present invention and to demonstrate the application of these embodiments in enhancing the performance of such an ablation system. Embodiments of the present invention, however, are by no means limited to this specific sort of example system, and the principles described herein may similarly be applied to other sorts of ablation systems.

Figure 2A:
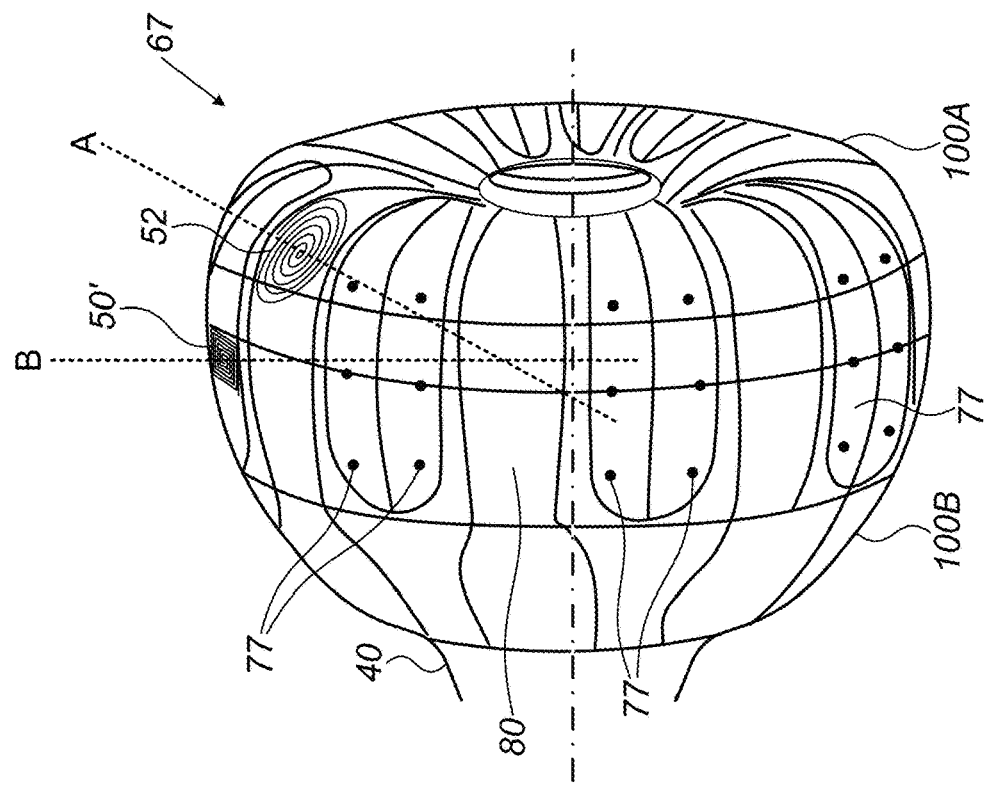
FIG. 2A is a schematic, pictorial illustration of a balloon coupled to a distal end of a catheter, in accordance with an embodiment of the present invention.

Ablation Balloon Catheter Having Diameter Smaller than 10 mm that Incorporates Temperature and Magnetic Position Sensors FIG. 2A is a schematic, pictorial illustration of balloon 66 coupled to catheter tip 40 at distal end 22a of catheter 21, in accordance with an embodiment of the invention.

In some embodiments, balloon 66 is typically in a collapsed position when physician 30 moves catheter tip 40 to the target location, and is configured to be inflated at the target location.

In the present example, at an inflated position, balloon 66 has a diameter of about 9 mm and comprising electrodes 77 disposed on the surface of balloon 66. In some embodiments, when placed in contact with tissue of heart 26, electrodes 77 are configured to sense intra-cardiac electrical signals from the tissue. In the example of FIG. 2, balloon 66 has multiple electrodes 77 so as to obtain high-resolution mapping of the electrical signals in tissue. In other embodiments, balloon 66 may have any other suitable diameter, typically but not necessarily, smaller than 10 mm.

In the context of the present disclosure and in the claims, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

In some embodiments, electrodes 77 are further configured to apply to the tissue, one or more RF ablation pulses received from RF generator 45 and controlled by processor 41 and/or by physician 30, as described in FIG. 1 above. In some embodiments, a large number of electrodes 77 disposed on the surface of balloon 66 provides physician 30 with several ablating configurations. For example, by applying the RF pulses using all electrodes 77 in contact with the tissue at the same, physician 30 may form a spatially-broad lesion. Alternatively, by using one or more electrodes 77 in contact with the tissue, physician 30 may obtain high-resolution ablation (e.g., form a narrow lesion) at one or more desired locations of the ablated tissue.

In some embodiments, physician 30 may determine the depth of lesion by controlling, inter alia, the energy and duration of RF ablation pulses applied to the tissue at the target location.

In some embodiments, balloon 66 may comprise a flexible substrate, such as but not limited to a flexible printed circuit board (PCB), having printed electrical interconnections. In the present example, the electrical interconnections comprise electrical traces 76, which are parallel to an axis 74 of catheter tip 40, and electrical traces 78, which are orthogonal to axis 74. The flexible PCB is wrapped around the surface of balloon 66, so that electrical traces 76 and 78 are configured to conduct electrical signals and/or RF ablation pulses between electrodes 77 and 50, and console 24.

In other embodiments, balloon 66 may comprise, in addition to or instead of electrical traces 76 and 78, electrical traces having any suitable orientation other than orthogonal or parallel to axis 74.

Reference is now made to an inset 60 showing spiral electrode (SE) 50. In some embodiments, SE 50 may comprise a coil 75, which is disposed on the surface of balloon 66, and is configured to output a signal indicative of the temperature of the tissue at the location of SE 50. Additionally or alternatively, in response to the magnetic fields produced by magnetic field generators 36, coil 75 of SE 50 is configured to output a signal indicative of the magnetic field, wherein the output signal is indicative of the position of balloon 66 in heart 26.

In principle, a balloon catheter having a diameter smaller than 10 mm, such as balloon 66, may comprise an impedance-based position sensor, such as in an Active Current Location (ACL) position racking system. In ACL, tracking the catheter is typically based on measuring impedances between the catheter, e.g., catheter tip 40, and external body electrodes, such as electrodes 38 described in FIG. 1 above. Each measurement is then translated into a respective position of the catheter within the body. The translation is typically based on a suitable mapping, which is constructed beforehand and translates an electrical impedance measured using the electrodes, into a respective position of the catheter. Such impedance-based position sensors may comprise any sort of coil, and therefore, are easy to implement in small-diameter balloons. However, the position sensing accuracy is typically less accurate compared to that of the aforementioned magnetic-based position sensor. Moreover, ACL may not provide with the orientation of catheter tip 40, which is particularly important in high-resolution mapping and ablation procedures.

In some embodiments, coil 75 of SE 50 has a first end 70 connected to electrical trace 76, and a second end 80 connected to electrical trace 78. Electrical traces 76 and are connected to wires running through shaft 22 to processor 41. Note that coil 75 may be formed on a layer different than that of at least one of electrical traces 76 and 78, and may be connected to predefined sections of traces 76 and 78 by an electrical plug referred to herein as a via. In the example shown in inset 60, trace 76 and coil 75 are formed in different layers, and therefore, are electrically connected at first end 70 of coil 75. If electrical trace 76 and coil 75 were formed in the same layer, then each winding of SE 50 was shorted to electrical trace 76, and therefore, SE 50 would have not been able to carry out the magnetic position sensing and/or the temperature sensing functions described above.

In the present example, coil 75 of SE 50 has a circular geometry, but in other embodiments, coil 75 may have any other suitable geometry, such as but not limited to a square geometry.

In some embodiments, the signal received from SE 50 may be processed by temperature sensing module 47, so as to determine the temperature of the tissue. In some embodiments, SE 50 may comprise an electrical resistance temperature detector (RTD), typically made from a pure material, such as platinum, nickel, or copper. The material of coil 75 has an accurate relationship between electrical resistance and temperature. In such embodiments, processor 41 is configured to hold data indicative of the resistance-temperature relationship, and based on the relationship, to provide an indication of the temperature of the ablated tissue. Note that SE 50 is further configured to measure the temperature of an electrode or any other component of balloon 66.

In alternative embodiments, in addition to or instead of one or more SEs 50, balloon 66 may comprise one or more thermocouples, which are coupled to the surface of balloon 66, and are configured to output an additional signal indicative of the temperature of the ablated tissue of heart 26.

In other embodiments, the signal received from SE 50 may be processed by processor 41, so as to determine the position of balloon 66 in the coordinate system of the magnetic position tracking system, or in any other suitable coordinate system of RF ablation system 20.

The configuration of spiral electrode 50 is provided by way of example, and the present invention is not limited to this particular configuration. For example, instead of coil 75, SE 50 may have a three-dimensional (3D) structure attached to the PCB or formed in the PCB. Moreover, SE 50 may be made from one or more coils, or from a coil having any other suitable shape, size and pitch.

Figure 2B:
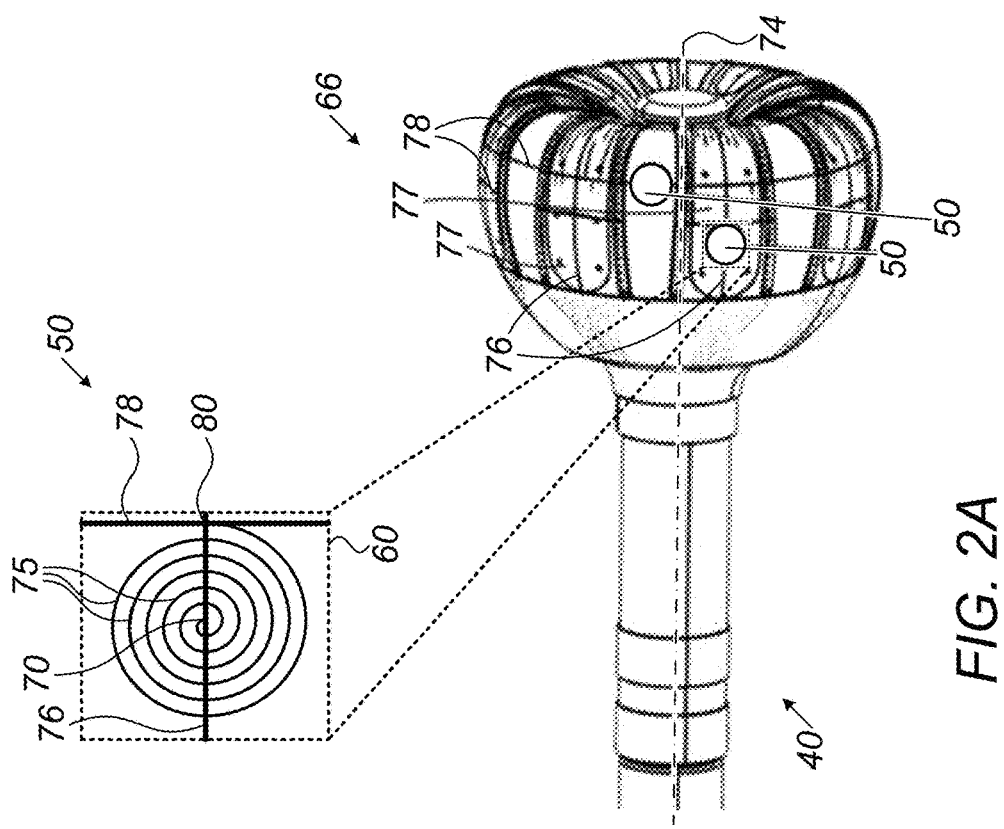
FIG. 2B is a schematic, pictorial illustration of a balloon coupled to a distal end of a catheter, in accordance with another embodiment of the present invention.

FIG. 2B is a schematic, pictorial illustration of a balloon 67, in accordance with another embodiment of the present invention. Balloon 67 may replace, for example, balloon 66 of FIGS. 1 and 2A.

In some embodiments, coil 75 may have any suitable shape other than spiral. As shown in the example of FIG. 2B, balloon 67 may comprise a coil 52, having a circular shape, and/or a coil 50' having a rectangular spiral shape. Moreover, instead of or in addition to coil 52, balloon 67 may comprise one or more electrodes having a serpentine-shaped trace or any other suitable shape as long as such shape allows for its intended purpose as a magnetic location sensor and/or thermocouple.

It should be noted that while coils 50' and 52 may be shown schematically as a coil disposed on a flat surface in FIG. 2A, in actual use the coil is disposed on a compound surface defined by the balloon membrane surface, shown here in FIG. 2B. In FIG. 2B, the membrane surface of balloon 67 can be seen as having two portions, a distal membrane portion 100A and a proximal membrane portion 100B. Distal membrane 100A can be considered to be a toroidal-like membrane in that distal portion 100A approximates the surfaces of a circular toroid. Proximal portion 100B, on the other hand, can be considered to be a hemispherical-like surface membrane in that it approximates a truncated hemispherical surface. Approximates here means that the surface of revolution of a toroid or a hemisphere can be overlaid onto the surface of the actual balloon membrane such that the surface of revolution for the toroid or the hemisphere will overlap with that of the actual balloon membrane.

In the configuration shown in FIG. 2B, coil 50' can be disposed above electrode 77 which is disposed on the compound surface of the membrane of balloon 67. Alternatively, coil 52 can be disposed below electrode 77, for example, between electrode 77 and the compound surface of the balloon. In the latter configuration, electrode 77 can be configured to have cut-outs to allow coil 52 to be exposed to the ambient environment, for the purpose of sensing temperature or avoiding electrical interference by electrode 77. Another coil location that can be utilized is that of the balloon membrane that is not occupied by an electrode. Coil 50' can be placed in on the membrane surface between any two electrodes 77. In one example, coil 50' can be placed in an empty surface 80 between two electrodes 77. In another example, a circular spiral coil of coil 52 is located on the balloon membrane so that coil overlaps both the toroid-like portion 100A and the hemisphere-like portion 100B while positioned in an area on the balloon not occupied by an electrode. As well, it is within the scope of the invention that coil 52 can be placed exclusively on either of the toroid-like portion 100A or the hemispherical portion 100B.

In FIG. 2B, coil 52 has an axis A that can extend at an angle to the longitudinal axis 74 of the balloon. Axis A may intersect with axis 74 but is not required. Coil 50' has an axis B that may be orthogonal to the longitudinal axis 74 but is not required to intersect axis 74.

Figure 3:
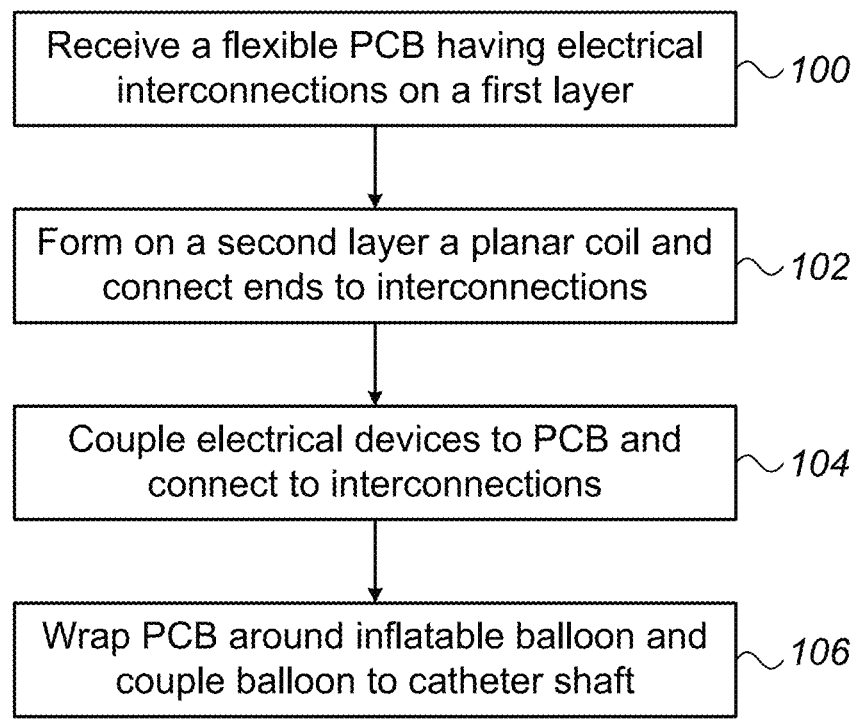
FIG. 3 is a flow chart that schematically illustrates a method for producing a catheter tip comprising a balloon, in accordance with an embodiment of the present invention.

FIG. 3 is a flow chart that schematically illustrates a method for producing catheter tip 40, in accordance with an embodiment of the invention. The method begins at a substrate receiving step 100 with receiving the flexible PCB substrate having electrical interconnections, such as but not limited to electrical traces 76 and 78, formed on a given layer, also referred to herein as a first layer of the PCB. In an embodiment, at least one of electrical traces 76 and 78 may be formed on another layer so as to produce a multi-level interconnection in the flexible PCB.

At a coil formation step 102, coil 75 of SE 50, which has a spiral shape, is formed on another layer, also referred to herein as a second layer, different from the first layer of the flexible PCB, so as to allow electrical interconnection of ends 70 and 80 to electrical traces 76 and 78, respectively. In other embodiments, coil 75 may be formed by printing a spiral-shaped trace (so as to produce spiral electrode 50), or any other suitable shape of the electrical trace, such as a serpentine-shaped trace, so as to form another electrode configured to carry out the magnetic position sensing and/or the temperature sensing functions described in FIG. 2 above.

At an electrical device coupling step 104, one or more electrical devices, such as but not limited to electrodes 77, and optionally, one or more thermocouples (instead of or in addition to one or more SEs 50), are coupled to flexible PCB and are connected to the electrical interconnections, such as one or more of electrical traces 76 and 78.

At a catheter tip assembling step 106 that concludes the method, the flexible PCB is wrapped around and coupled to balloon 66 (e.g., using bonding or soldering), and balloon 66 is coupled to distal end 22a of shaft 22 so as to complete the formation of catheter tip 40.

The configuration of catheter tip 40 and the production method thereof are simplified and described for the sake of conceptual clarity so as to show the key features of the disclosed invention.

Although the embodiments described herein mainly address sensing and ablating cardiac tissue using a balloon catheter having diameter smaller than 10 mm, the methods and systems described herein can also be used, mutatis mutandis, in other applications, such as in sensing and ablating tissue other cardiac using a balloon catheter having any suitable diameter.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A catheter, comprising:
an inflatable balloon for insertion into an organ of a patient;
a flexible substrate comprising a first layer and a second layer and wrapped around the inflatable balloon;
electrical interconnections formed on the first layer;
one or more electrodes, disposed on a surface of the inflatable balloon and configured to be placed in contact with tissue of the organ, and to perform at least one of: (i) sensing one or more electrical signals from the tissue, and (ii) applying one or more ablation pulses to the tissue; and
one spiral-shaped coil, disposed on the second layer, that spirals radially outward from a first end to a second end, the first end of the coil being connected to a first electrical trace of the electrical interconnections and the second end of the coil being connected to a second electrical trace of the electrical interconnections that extends orthogonally relative to the first electrical trace, wherein the coil is configured to output a signal indicative of: (i) a temperature of the tissue, and (ii) a magnetic field indicative of a position of the catheter in the organ.

2. The catheter according to claim 1, wherein the inflatable balloon has a diameter smaller than 10 mm at an inflated position.

3. The catheter according to claim 1, wherein the one coil comprises a magnetic sensor, which is configured to sense the magnetic field for sensing the position of the catheter in the organ.

4. The catheter according to claim 1, wherein the one coil comprises a resistance temperature detector (RTD), which is configured to output the signal indicative of the temperature of the tissue.

5. The catheter according to claim 1, further comprising one or more thermocouples, which are coupled to the surface of the inflatable balloon, and are configured to output an additional signal indicative of the temperature of the tissue.

6. The catheter according to claim 1, the flexible substrate being a flexible printed circuit board (PCB).

7. The catheter according to claim 6, wherein the one or more electrodes and the one coil are connected to electrical traces of the flexible PCB.

8. The catheter according to claim 1, wherein the first end of the one coil is connected to the first electrical trace by a via.

9. A method for producing a catheter, the method comprising:
receiving a flexible substrate comprising electrical interconnections formed on a first layer of the flexible substrate;
forming, on a second layer of the flexible substrate, one spiral-shaped coil that spirals radially outward from a first end to a second end, and connecting the first end to a first electrical trace of the electrical interconnections and the second end to a second electrical trace of the electrical interconnections that extends orthogonally relative to the first electrical trace, and the one coil is configured to output a signal indicative of: (i) a temperature of tissue, and (ii) a magnetic field indicative of a position of the catheter in an organ;
coupling one or more electrical devices to the flexible substrate and connecting each of the one or more electrical devices to a respective electrical interconnection of the electrical interconnections; and
wrapping the flexible substrate around an inflatable balloon, and coupling the inflatable balloon to a distal end of a shaft of the catheter.

10. The method according to claim 9, wherein receiving the flexible substrate comprises receiving a printed circuit board (PCB), and wherein the electrical interconnections comprise electrical traces of the PCB.

11. The method according to claim 9, wherein coupling the one or more electrical devices comprises coupling at least one of: (i) one or more electrodes, and (ii) one or more thermocouples.

12. The method according to claim 9, wherein the first end of the one coil is connected to the first electrical trace by a via.

13. A catheter, comprising:
an expandable balloon defining a longitudinal axis extending through the balloon, the balloon having a compound curved surface of revolution about the longitudinal axis;
a flexible substrate comprising a first layer and a second layer and wrapped around the expandable balloon;
electrical interconnections formed on the first layer;
one or more electrodes, disposed on the compound curved surface of the expandable balloon and configured to be placed in contact with tissue of an organ, and to perform at least one of: (i) sensing one or more electrical signals from the tissue, and (ii) applying one or more ablation pulses to the tissue; and
one spiral-shaped coil, disposed on the second layer, spiraling radially outward from a first end to a second end and defining a coil axis extending at an angle to the longitudinal axis of the balloon, the first end of the one coil being connected to a first electrical trace of the electrical interconnections and the second end of the one coil being connected to a second electrical trace of the electrical interconnections that extends orthogonally relative to the first electrical trace, wherein the one coil is configured to output a signal indicative of: (i) a temperature of the tissue, and (ii) a magnetic field indicative of a position of the catheter in the organ.

14. The catheter according to claim 13, wherein the balloon comprises a distal toroidal-like surface portion approximating a circular toroid and a proximal hemisphere-like surface portion approximating a truncated hemispherical surface, the one coil being disposed on the compound curved surface, the toroidal-like surface portion, and the hemisphere-like surface portion of the balloon.

15. The catheter according to claim 13, wherein the one coil is disposed on the compound curved surface of the balloon that does not have the one or more electrodes mounted thereon.

16. The catheter according to claim 13, wherein the one coil is disposed between the one or more electrodes and the compound curved surface of the balloon.

17. The catheter according to claim 16, wherein the one or more electrodes includes cut outs to allow the one coil under the one or more electrodes to be exposed to the ambient environment.

18. The catheter according to claim 16, wherein the first end of the one coil is connected to the first electrical trace by a via.

* * * * *